United States Patent [19]

Hemberger et al.

[11] Patent Number: 5,710,131
[45] Date of Patent: Jan. 20, 1998

[54] INHIBITOR OF COLLAGEN-STIMULATED PLATELET AGGREGATION

[75] Inventors: Jürgen Hemberger, Aschaffenburg; Guido Melzer, Hofheim/Ts., both of Germany

[73] Assignee: Merck Patent Gesellschaft Mit Beschrankter Haftung, Darmstadt, Germany

[21] Appl. No.: 392,970

[22] PCT Filed: Jun. 28, 1994

[86] PCT No.: PCT/EP94/02087

§ 371 Date: Feb. 28, 1995

§ 102(e) Date: Feb. 28, 1995

[87] PCT Pub. No.: WO95/01375

PCT Pub. Date: Jan. 12, 1995

[30] Foreign Application Priority Data

Jul. 1, 1993 [DE] Germany .................. 93110528.2

[51] Int. Cl.$^6$ .................. A61K 38/00; C07K 1/00
[52] U.S. Cl. .................. 514/21; 514/822; 530/350; 530/380; 530/855; 530/858; 424/532; 424/537; 424/550
[58] Field of Search .................. 514/21, 822; 530/350, 530/380, 855, 858; 424/532, 537, 550

[56] References Cited

U.S. PATENT DOCUMENTS

| | | | |
|---|---|---|---|
| 5,182,113 | 1/1993 | Rigbi et al. | 424/537 |
| 5,238,919 | 8/1993 | Zimmerman et al. | 514/8 |
| 5,256,559 | 10/1993 | Maragauore et al. | 435/240.2 |
| 5,342,830 | 8/1994 | Scarborough | 514/12 |

FOREIGN PATENT DOCUMENTS

| | | |
|---|---|---|
| A0 255 206 | 2/1988 | European Pat. Off. . |
| A0 372 670 | 6/1990 | European Pat. Off. . |
| A0 384 362 | 8/1990 | European Pat. Off. . |
| 0480651 | 4/1992 | European Pat. Off. . |
| A0 480 651 | 4/1992 | European Pat. Off. . |
| WO92 08472 | 5/1992 | WIPO . |

OTHER PUBLICATIONS

Journal of Biological Chemistry, vol. 267, No. 10, 5 Apr. 1992 (Baltimore, Maryland, pp. 6893–6898.
Orevi et al, *Prostaglandins*, vol. 43, pp. 483–495, 1992.
Harsfalvi et al, *Blood*, vol. 85, No. 3, pp. 705–711, Feb. 1, 1995.
Deckmyn et al, *Blood*, vol. 85, No. 3 pp. 712–719, Feb. 1, 1995.

*Primary Examiner*—Cecilia Tsang
*Assistant Examiner*—Abdel A. Mohamed
*Attorney, Agent, or Firm*—Millen, White, Zelano & Branigan, P.C.

[57] ABSTRACT

A protein isolated from crude extracts of *Hirudo medicinalis* is disclosed, which strongly inhibits the binding to collagen of platelets and their subsequent activation, which leads to platelet aggregation and thrombus formation. Additionally the protein prevents binding of von Willebrand factor to collagen. Described is a method for isolation and purification of the protein as well as its use for blocking collagen-stimulated platelet aggregation. The new protein (Brandinin) has a molweight of approximately 15 kD, binds to collagen but has no collagen-cleaving activity. The protein is useful in the prophylaxis, prevention and treatment of thrombotic diseaeses and for coating of blood-contacting materials, rendering them thromboresistant.

9 Claims, 4 Drawing Sheets

INHIBITOR OF COLLAGEN-STIMULATED PLATELET AGGREGATION

The present invention is concerned with a new protein acting as strong inhibitor of collagen-stimulated platelet activation and aggregation and, above all, having a capacity to prevent interactions between collagen and von Willebrand's factor.

Normal hemostasis in humans is regulated by a complex series of interrelated mechanisms involving both cellular and humoral biochemical components. The biochemical pathway involves injury to intact endothelial cells, stimulation of platelets and activation of coagulation mechanisms. When a vessel wall is damaged, one of the first events is the exposure of subendothelium to the blood. Subendothelial collagen is thought to be one of the very first stimuli that lead to adhesion of platelets, followed by shape change, aggregation and thrombus formation.

Therefore therapeutic intervention at the level of platelet adhesion and/or platelet aggregation is useful for the prevention or treatment of most thrombotic disorders.

It is known that leech salvia contains several agents capable of inhibiting platelet aggregation:

Thus, hirudin is a well known compound (Merck Index 1983, No. 4613; FEBS Lett. 165, 180 (1984)). Hirudin prevents thrombin-induced platelet aggregation by binding to thrombin in a 1:1 stoichiometric complex. This in turn inhibits thrombin-catalysed conversion of fibrinogen to fibrin.

A low molecular weight receptor-mediated platelet activating factor antagonist derived from saliva of Hirudinidae having inhibitory activity against platelet aggregation induced by aggregation agents such as PAF-acether is disclosed in EP-A-0348208.

A collagenase which specifically degrades collagen by means of hydrolytic scission of peptide bonds in helical regions of the collagen molecule is disclosed in WO 87/00860.

The medicinal leech (*Hirudo medicinalis*) uses not only hirudin to prevent thrombus formation at the site of a bite. A very pronounced characteristic of a bite from this leech is prolonged bleeding for more than 10 up to 24 hrs, whereas hirudin appears to be washed out of the wound within 15 to 30 min. Therefore other principles apart from hirudin must be responsible for this effect.

Recently a protein from *Hirudo medicinalis* was described (WO 92/07005) having a molecular weight of 65 kD and termed "Calin", which is able to prevent collagen-stimulated platelet aggregation.

Another low molecular (16 kD) inhibitor of collagen-induced platelet aggregation, termed LAPP, was found in *Haementeria officinalis* (EP-A-0480651).

None of these proteins have been shown to affect the important feature of von Willebrand's factor (vWF) mediated platelet adhesion.

This factor is a complex multimeric glycoprotein that plays an essential role in platelet function. It is required for normal platelet adhesion to exposed subendothelium and for normal platelet plug formation at sites of vascular injury.

The function of vWF is particularly important in vessels of small caliber, where conditions of high wall shear rate prevail. It is now recognized that the mechanisms underlying vWF function comprise interaction with components of the subendothelium as well as with specific receptors on the platelet membrane (Ruggeri et al., 1992, Meth. Enz. 215, 263–275).

Therefore, interference of a corresponding protein with vWF would provide an additional advantage in therapeutic uses.

Now it has been found that a new protein having a molecular weight about 15 kD acts as strong inhibitor of collagen-stimulated platelet aggregation and adhesion and, above all, prevents interactions between collagen and vWF.

Therefore, it is an object of the present invention to provide a substantially pure protein having a capacity to inhibit collagen-stimulated platelet aggregation and to prevent interactions between collagen and vWF, obtainable from the saliva of the medicinal leech *Hirudo medicinalis*.

The new protein according to the invention has a molecular weight of 14–15.5 kD, preferrably of 14.5–15.0 (dependent oh the used methods) and prevents interactions between collagen and vWF. In contrast to these results, the known LAPP has a molecular weight of 16 kD and has been isolated from *Haementeria officinalis*. An influence of LAPP on vWF could not be demonstrated up to now. Another important feature is that the amino acid sequences of LAPP and the protein according to the invention (Brandinin) are different.

These and other differences exemplified below, differentiate the protein according to this invention from other proteins having inhibitory activity on platelet aggregation.

The protein of the present invention includes variations of the disclosed purified protein which conserve the activity of the isolated protein, including fragments, subunits, naturally occurring mutations and randomly generated artificial mutants. Also included are hybrid proteins such as fusion proteins deriving from the disclosed protein.

Furthermore, the present invention relates to a method for preparing the novel protein using known standard techniques per se.

Thus, it is an object of the invention to provide a process for the production of a substantially pure protein having a capacity to inhibit collagen-stimulated platelet aggregation and to prevent interactions between collagen and von Willebrand's factor and having a molucular weight of 14 to 15.5 kD, characterized in that it is isolated and purified, optionally by a one-step-purification by preparative electrophoresis, from the saliva of the medicinal leech *Hirudo medicinalis*.

A typical process according to the invention involves reconstitution of lyophilized crude saliva of *Hirudo medicinalis* in a conventional buffer system at pH 7.5–8.5 and purification by at least one conventional chromatograpy step, preferrably gel permeation chromatography.

Additionally, the present invention relates to pharmaceutical formulations and medical devices.

Thus, it is a further object of the invention to provide a pharmaceutical formulation comprising as active ingredient a protein as defined above and in the claims, associated with one or more pharmaceutically acceptable carriers, excipients or diluents therefor.

The pharmaceutical formulations according to the invention optionally may comprise additional active ingredients like anti-coagulants such as hirudin or heparin or thrombolytic agents such as plasminogen activator or hementin.

The new protein and the pharmaceutical formulations of the present invention, respectively, may be used for the treatment of various thromoembolic disorders, including venous thrombosis, peripheral arterial thrombosis, cerebrovascular thrombosis and myocardial infarction, as well as for patients with arteriovenous shunts, or undergoing coronary bypass surgery. The formulations may also be used for the treatment of autoimmune disease, including lupus erythematosus, rheumatoid arthritis and polyarthritis nodosa. The formulations of this invention are also useful in simulating the prolonged bleeding phenomenon experienced after leech bites and may therefore substitute, entirely or in part, for the leech in those applications which are currently indicated for leech therapy.

The novel protein according to the invention may form parmaceutically acceptable salts with any non-toxic, organic or inorganic acid. Inorganic acids are, for example, hydrochloric, hydrobromic, sulphuric or phosphoric acid and acid metal salts such as sodium monohydrogen orthophosphate and potassium hydrogen sulfate. Examples for organic acids are the mono, di and tri carboxylic acids such as acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic and sulfonic acids such as methane sulfonic acid. Salts of the carboxy terminal amino acid moiety include the non-toxic carboxylic acid salts formed with any suitable inorganic or organic bases. These salts include, for example, alkali metals such as sodium and potassium, alkaline earth metals such as calcium and magnesium, light metals of Group IIIA including aluminium, and organic primary, secondary and tertiary amines such as trialkylamines, including triethylamine, procaine, dibenzylamine, 1-ethenamine, N,N'-dibenzylethylene-diamine, dihydroabietylamine and N-alkylpiperidine.

The formulations according to the invention may be administered as unit doses containing conventional non-toxic pharmaceutically acceptable carriers, diluents, adjuvants and vehicles which are typical for parenteral administration. The term "parenteral" includes herein subcutaneous, intravenous, intra-articular and intratracheal injection and infusion techniques. Unit doses according to the invention may contain daily required amounts of the protein according to the invention, or sub-multiples thereof to make up the desired dose. The optimum therapeutically acceptable dose for a given patient (mammals, including humans) depends on a variety of factors, such as the activity of the specific active material employed, the age, body weight, general health, sex, diet, time and route of administration, rate of clearance and so on. Therefore, the necessary blood concentration which inhibits stimulation of platelet aggregation by collagen is preferrably within a range of 0.1 mg/l–50 mg/l.

As used herein, the term "pharmaceutically acceptable carrier" means an inert, non toxic solid or liquid filler, diluent or encapsulating material, not reacting adversely with the active compound or with the patient. Suitable, preferrably liquid carriers are well known in the art such as steril water, saline, aqueous dextrose, sugar solutions, ethanol, glycols and oils, including those of petroleum, animal, vegetable, or synthetic origin, for example, peanut oil, soybean oil and mineral oil. Carriers according to the invention are also pharmaceutically acceptable gels or creams, suitable for coating, prior to use, medical devices which are commonly made from plastics materials and synthetic fibres (see below).

It is also object of this invention to provide an implantable or extracorporal medical device for use in contact with body fluids in order to render the device surface substantially thromboresistant, coated with an immobilized protein as defined above and in the claims. The protein according to the invention is immobilzed on a medical device so as to render the surface biocompatible and thromboresistant. Such devices sometimes have wettable surfaces which typically induce platelet aggregation, which is a disadvantage in their intended uses in inplantable and extracorporeal devices in contact with blood or other body fluids. Example for such devices are protheses, artificial organs, sutures, artificial vascular segments, catheters, dialysers, tubes and vessels carrying blood.

The methods of coating the medical devices and immobilizing proteins are performed according to standard techniques (e.g. U.S. Pat. No. 4,885,207).

Finally, the present invention relates to the use of a protein as defined above and in the claims for the manufacture of a medicament for the prevention of collagen-stimulated platelet aggregation and binding of vWF to collagen in vitro, in vivo and for extracorporal treatments.

EXAMPLE 1

In Vitro-Activity of the Protein from *Hirudo medicinalis* as Inhibitor of Collagen-stimulated, Platelet Aggregation In the crude saliva of *Hirudo medicinalis* activity can be detected, that inhibits in a dose dependent manner aggregation of platelets in platelet-rich plasma (PRP), caused by the presence of collagen.

Blood was withdrawn from volunteers with sodium citrate with a final concentration of 0.38%. Platelet rich and platelet poor plasma were prepared by differential centrifugation.

Platelet aggregation was performed in the aggregometer PAP-4 (Biodata) by adding different concentrations of collagen horm® (Hormonchemie). Parameter was the maximal extinction after addition of collagen. Antithrombotics decrease the values.

The assay described above, was used throughout to following purification of the protein and for characterization of the pure protein according to this invention, respectively.

EXAMPLE 2

Isolation and Chromatographic Purification of the Protein

Figure 1:
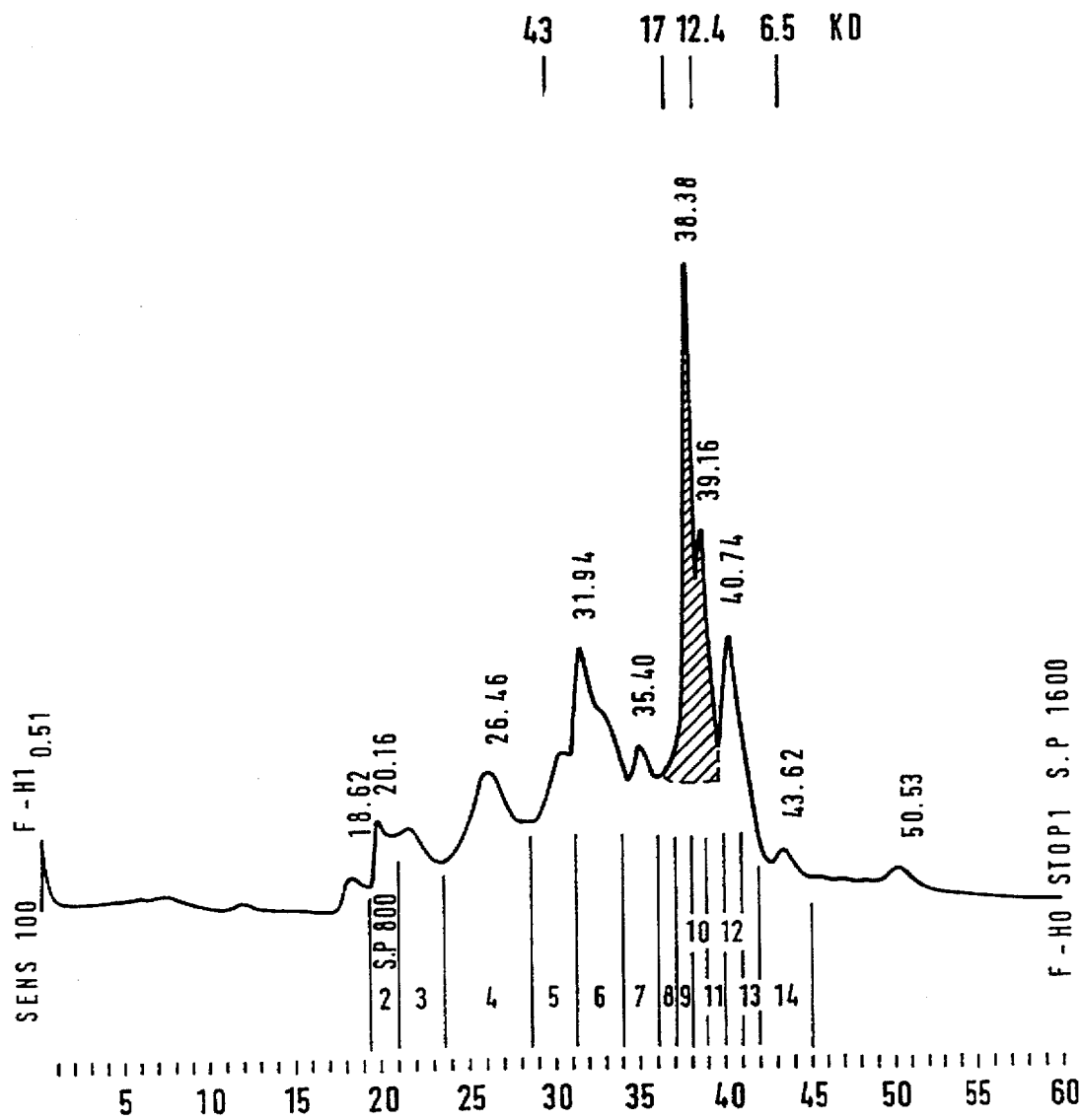
FIG. 1: Purification of Brandinin from leech saliva by gel permeation chromtography. Details are given in Example 2. The dark hatched regions indicate the active fractions. The numbers below the curve (3–14) indicate the fractions.

The protein according to the invention could be isolated from crude saliva of *Hirudo medicinalis*. Lyophilized saliva was reconstituted in 20 mM Tris-HCl, 10 mM $CaCl_2$ pH 8.0 (TC-buffer) at a concentration of 20 mg/ml. The saliva was loaded onto a CM-Fraktogel® column (E. Merck, Darmstadt, FRG) ) and eluted with a NaCl-gradient in the same buffer. The column fractions active in the platelet-inhibition-assay described in example 1, contained no more hirudin activity. Final purification was performed by gel permeation chromatography on a diol-modified silica-column in 20 mM Tris-HCl, 10 mM $CaCl_2$, 200 mM NaCl pH 8.0 (TCN-buffer). A typical example of this purification step is depicted in FIG. 1. The yield of purified protein compared with the protein amount of the crude saliva was 5%. In other experiments yields between 2 and 7% were obtained.

EXAMPLE 3

One-Step Purification of the Protein by Preparative Electrophoresis

Alternatively the protein could be successfully isolated in one step by preparative electrophoresis. Into the "Prep-cell"® apparatus (Biorad, Munich, FRG) a cylindrical polyacrylamide gel with typically 10% acrylamide was polymerized following the instructions of the manufacturer. Sample was applied in electrophoresis buffer. During electrophoresis a buffer stream rectangular to the electrophoresis direction served to transport eluted proteins to a fraction collector. The fractions were analyzed by analytical SDS-polyacrylamide electrophoresis and pooled according to the molecular weight of 15.0 kD. In another varified experiment a molecular weight value was destinated of 14.5 kD.

EXAMPLE 4

Characterization of the Protein

Figure 2:
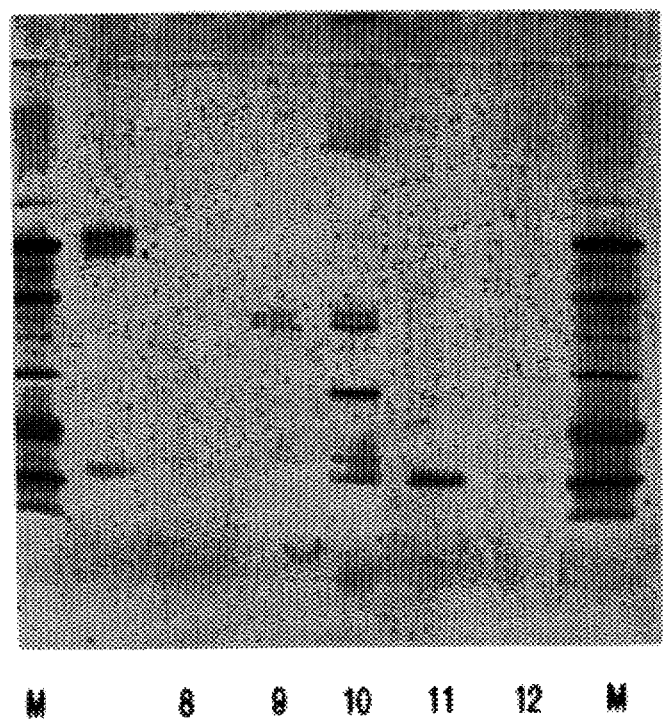
FIG. 2: Purification of Brandinin by SDS-gel electrophoresis. Details are given in Example 4. Indicated are the fraction numbers (8–12) and markers (M). Fractions 10 and 11 are positive in the assay according to Example 1.

The purified protein having activity according to example 1 showed a molecular weight of approximately 15000 D in SDS-PAGE under reducing conditions. FIG. 2 depicts active fractions from a typical gel permeation chromatography described in Example 2. Protein bands on the gel were visualized by silver staining.

With the purified protein we were not able to detect any proteolytic activity using a preferred assay method described below. Casein covalently modified by resorufin® (Boehringer, Mannheim, FRG) was used as substrate with proteinase K as positive control. To 50 µl of a solution of 0.4% casein resorufin-labeled 50 µl of 200 mM Tris, 20 mM CaCl2 pH 7.8 and 100 µl sample solution were added. After incubation for up to 24 hrs at 37° C., the reaction was stopped by adding 450 µl of a 5% solution of trichloroacetic acid. The reaction mix was centrifuged and 400 µl of the supernatant transferred to a cuvette containing 600 µl 500 mM Tris pH 8.8 The absorbance at 574 nm was read immediately. Incubations for 24 hrs showed significant proteolytic activity in the crude saliva, whereas in the case of the purified protein absorbance values slightly below background levels were observed (Tab. 1, see below).

Figure 3:
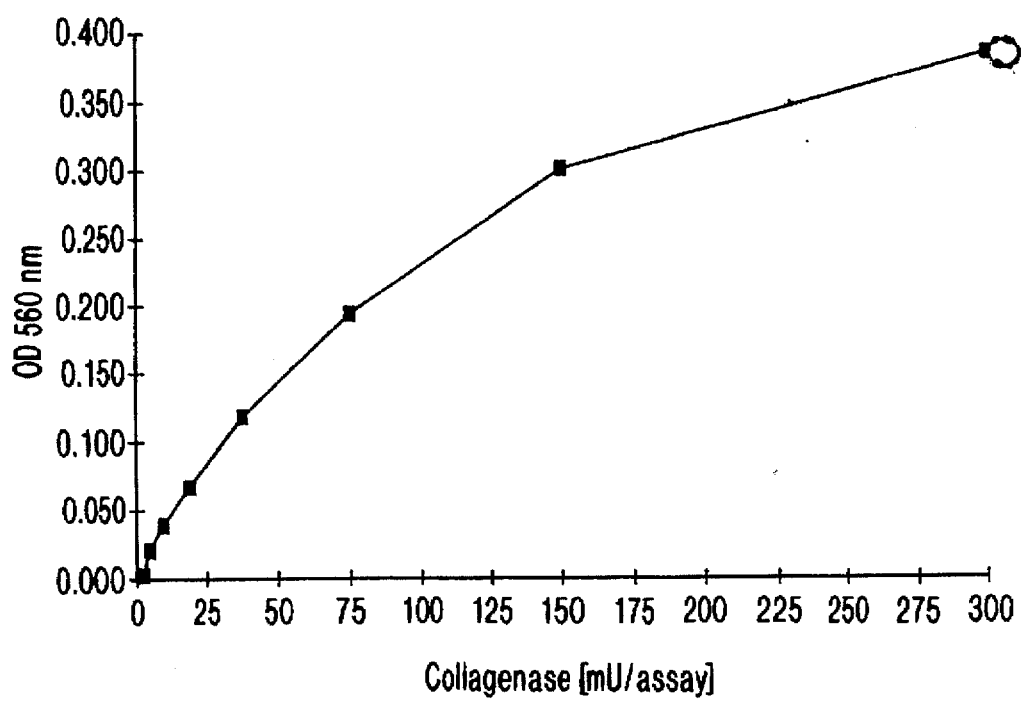
FIG. 3: Standard curve of collagenolytic activity measured by Azocoll®. Details are given in Example 4. Vertical axis: optical density (OD) at 560 nm; horizontal axis: collagenase activitiy (mU/assay).

Besides the proteolytic activity, described above, crude saliva also has collagenolytic activity. A preferred method for measuring this activity is the use of azocoll, a non-specific chromogenic collagenase substrate, in following way. Azocoll® (Calbiochem) was suspended in 50 mM Tris, 200 mM NaCl, 0.1% Brij 35, 0.01% $NaN_3$ pH 8.0 (buffer A) at a concentration of 20 mg/ml and washed twice by centrifugation, aspiration and resuspension. 100 µl of sample or buffer control were pipetted into wells of a 96-well microtiterplate as dilution series in buffer A, followed by 100 µl azocoll suspension. This mixture was incubated at 37° C. for typically 18 hrs. To stop the reaction, undigested substrate was sedimented by centrifugation at 1000 xg for 10 min. Supernatants were transferred to a new microtiterplate and the absorbance was read at 560 nm. Collagenase from Clostridium histolyticum (Sigma) was used to prepare standard curves (FIG. 3).

TABLE 1

Proteolytic Activity in Saliva and Purified Protein

|  | OD (574 nm) | OD - control |
| --- | --- | --- |
| buffer | 0.0592 +/- 0.0013 | 0 |
| saliva (5.0 µg/ml) | 0.0761 +/- 0.0014 | 0.0169 |
| Brandinin (37 µg/ml) | 0.0522 +/- 0.0001 | -0.0070 |
| proteinase K (0.5 µg/ml) | 1.5572 +/- 0.1429 | 1.4980 | means +/- standard deviation, n = 3 experiments

Tab. 2 contains the results of typical measurements using this assay. In contrast to crude saliva and another hirudo protein named Calin (WO 92/07005), which showed activity in the azocoll assay, it was surprisingly found that the purified protein according to this invention had no significant collagenolytic activity above background levels.

TABLE 2

Collagenolytic Activity in the Azocoll Assay

|  | Protein [µg/assay] | OD(560 nm) after 18 hrs. | Azocoll Activity [mU/assay] | spec. Activity [mU/µg] |
| --- | --- | --- | --- | --- |
| Saliva | 2.10 | 0.1090 | 54.5 | 26.0 |
| Calin | 0.74 | 0.0966 | 48.3 | 65.3 |
| Purified Protein | 1.80 | 0.0030 | 1.5 | 0.8 |

EXAMPLE 5

Dose-dependent Inhibition of Platelet Aggregation by Purified Protein

Figure 4A:
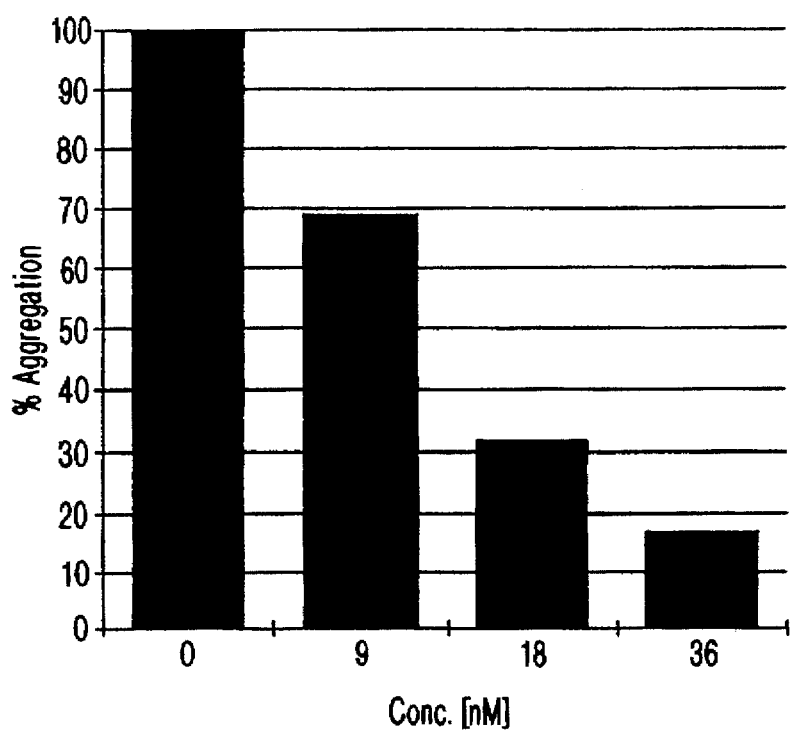
FIG. 4a: Dose-dependent inhibition of collagen-stimulated platelet aggregation. Details are given in Example 5. Vertical axis: % of aggregation, horizontal axis: concentration of Brandinin (nM).
Figure 4B:
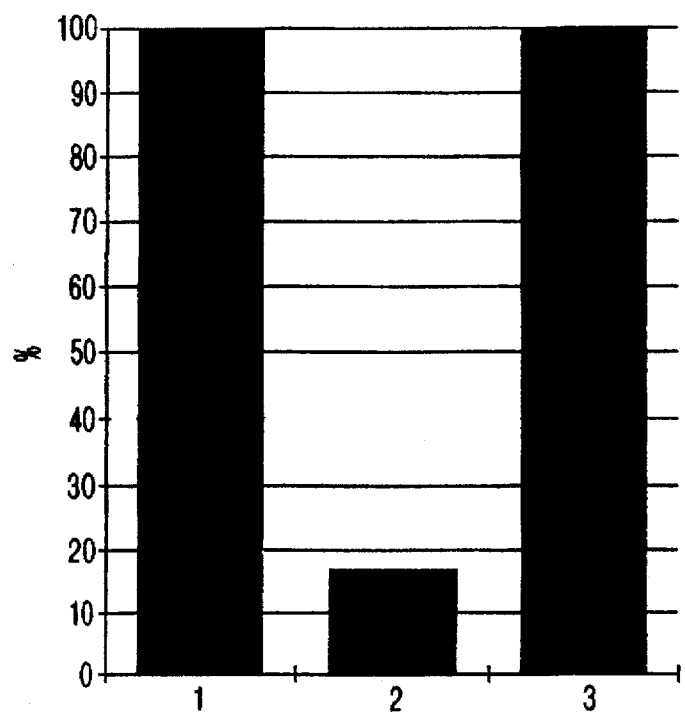
FIG. 4b: Collagen specificity of inhibition of platelet aggregation. Details are given in Example 5. Vertical axis: % of aggregation, horizontal axis: 1=control, 2=collagen, 3=ADP.

Platelet rich plasma was incubated for 2 minutes at 37° C. with the test compound and aggregated by addition of collagen to a final concentration of 1.25 ug/ml. The protein of this invention (Brandinin) showed an $IC_{50}$ of about 15 nM. In further experiments results between 0.5 and 100 nM were obtained. Crude extract of saliva showed inhibition of collagen-stimulated as well as ADP-stimulated platelet aggregation. In contrast, Brandinin was ineffective in the highest available concentration. Details can be seen from FIGS. 4a and 4b.

EXAMPLE 6

Inhibition of vWF-Binding to Collagen in Vitro by the Purified Protein

Besides inhibiting the direct interaction of platelets with collagen, the purified protein according to this invention, has the surprising additional ability to interfere with the binding of vWF.

This was shown by coating 96-well microtiter plates with 5 µg collagen type I from equine tendon per well. Collagen was dissolved in 0.1M acetic, acid and dialysed for 18 hrs.

against phosphate buffer pH 7.2. After incubation for 1 hr. at 37° C., wells were blocked by 250 µl of 10 mg/ml BSA in PBS buffer and washed three times with BSA-free PBS buffer. 25 µl sample containing the protein according to this invention was added followed by 75 µl human plasma diluted 1:80 in PBS containing 5 mM EDTA, 0.1% BSA, 0.001% Tween 80 PH 7.4 and incubated for 2 hrs. at 37° C. After washing again, bound vWF was detected by 100 µl of 1/4000 diluted polyclonal rabbit anti-vWF antiserum conjugated to horse radish peroxidase (Dako, Copenhagen, Denmark). The antiserum was incubated for 1 hr. at 37° C. Colour development was done with ABTS for 30 min at 37° C., measurement was at 405 nm. In some experiments purified vWF factor (Serbio, Remagen, FRG) instead of human plasma was used, with very similar results compared to the plasma measurement.

Figure 5:
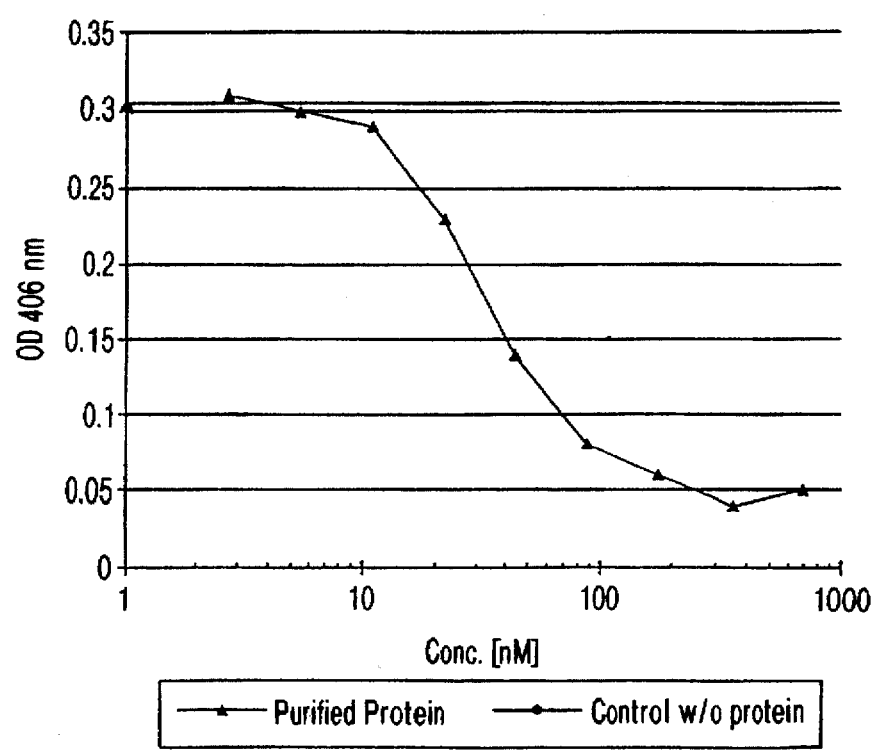
FIG. 5: Dose-dependent inhibition of vWF-binding to collagen. Details are given in Example 6. Vertical axis: optical density (OD) at 405 nm; horizontal axis: concentration of purified protein (nM). . . . . ▲ . . . . purified protein; . . . . ● . . . . control w/o protein The following examples describe the present invention in more details.

Binding of vWF both from plasma and in purified form could be prevented by Brandinin, the purified protein according to this invention in a dose-dependent manner. 50% inhibition under standard conditions was approximately 40 nM (Range 0.5 nM to 100 nM) (FIG. 5).

By binding to collagen Brandinin comprises not only the inhibition of the interaction of platelets with collagen, but also the binding of von Willebrand factor to this subendothelial matrix component.

We claim:

1. A substantially pure protein which inhibits collagen-stimulated platelet aggregation and to prevent interactions between collagen and von Willebrand's factor (vWF), obtainable from the saliva of the medicinal leech *Hirudo medicinalis*.

2. Protein according to claim 1, having a molecular weight of 14 to 15.5 kD in SDS-PAGE under reducing conditions.

3. A method for the preparation of a medicament for the prevention of platelet aggregation or binding of von Willebrand's factor (vWF) to collagen in vitro, in vivo and for extracorporal treatment which comprises a protein of claim 1 with a pharmaceutical acceptable carrier, excipient or diluent.

4. A pharmaceutical formulation comprising as active ingredient a protein according to claim 1, and additionally comprising one or more pharmaceutically acceptable carriers, excipients or diluents therefor.

5. A pharmaceutical formulation according to claim 4 further comprising a thrombolytic agent or anti-coagulant.

6. A pharmaceutical formulation according to claim 4, wherein the pharmaceutically acceptable carrier comprises a gel base or cream, suitable for coating, prior to use, a medical device.

7. A process for the production of a substantially pure protein having a capacity to inhibit collagen-stimulated platelet aggregation and to prevent interactions between collagen and von Willebrand's factor (vWF) and having a molucular weight of 14 to 15.5 kilodaltons in SDS-PAGE under reducing conditions, wherein it is isolated and purified from the saliva of the medicinal leech *Hirudo medicinalis*.

8. A process according to claim 7, wherein the protein is isolated from the crude material in one step by preparative electrophoresis.

9. A substantially pure protein isolated from the saliva of the medical leech *Hirudo medicinalis* which:

i) has a molecular weight of 14–15.5 kilodaltons in SDS-PAGE under reducing conditions, ii) inhibits collagen-stimulated platelet aggregation, iii) inhibits collagen-stimulated platelet adhesion to collagen, iv) prevents interactions between collagen and von Willebrand's factor (vWF), v) has no collagenolytic activity, and vi) binds to collagen.

* * * * *